United States Patent
Somasundaram et al.

(10) Patent No.: US 10,192,003 B2
(45) Date of Patent: Jan. 29, 2019

(54) METHOD OF ALIGNING INTRA-ORAL DIGITAL 3D MODELS

(71) Applicant: 3M INNOVATIVE PROPERTIES COMPANY, St. Paul, MN (US)

(72) Inventors: Guruprasad Somasundaram, Minneapolis, MN (US); Evan J. Ribnick, St. Louis Park, MN (US); Ravishankar Sivalingam, Woodbury, MN (US); Shannon D. Scott, Hudson, WI (US); Golshan Golnari, Minneapolis, MN (US); Aya Eid, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 681 days.

(21) Appl. No.: 14/479,692

(22) Filed: Sep. 8, 2014

(65) Prior Publication Data

US 2016/0070821 A1 Mar. 10, 2016

(51) Int. Cl.
| | | |
|---|---|---|
| G06F 3/00 | (2006.01) | |
| G06F 17/50 | (2006.01) | |
| A61C 9/00 | (2006.01) | |
| A61C 13/00 | (2006.01) | |
| A61C 7/00 | (2006.01) | |

(52) U.S. Cl.
CPC ........... *G06F 17/50* (2013.01); *A61C 7/00* (2013.01); *A61C 9/004* (2013.01); *A61C 13/0004* (2013.01); *A61C 2007/004* (2013.01)

(58) Field of Classification Search
CPC .................. G06F 17/50; G06F 17/60
USPC ............................................. 703/1
See application file for complete search history.

(56) References Cited

U.S. PATENT DOCUMENTS

| | | | |
|---|---|---|---|
| 7,077,647 B2 | 7/2006 | Choi | |
| 7,220,122 B2 | 5/2007 | Chishti | |
| 7,442,041 B2 | 10/2008 | Imgrund | |
| 7,471,821 B2 | 12/2008 | Rubbert | |
| 7,605,817 B2 | 10/2009 | Zhang | |
| 7,695,278 B2 | 4/2010 | Sporbert | |
| 7,826,646 B2 | 11/2010 | Pavlovskaia | |
| 7,956,862 B2 | 6/2011 | Zhang | |
| 8,075,306 B2 | 12/2011 | Kitching | |
| 8,244,028 B2 | 8/2012 | Kuo | |
| 8,275,180 B2 | 9/2012 | Kuo | |
| 8,573,972 B2 * | 11/2013 | Matov | A61C 7/08 433/196 |

(Continued)

FOREIGN PATENT DOCUMENTS

JP 2003296378 10/2003

OTHER PUBLICATIONS

Peter, Geometrical closing of 3 D object via simultaneous registration of multiple (Year: 1997).*

(Continued)

*Primary Examiner* — Lechi Truong

(57) ABSTRACT

Methods for aligning a digital 3D model of teeth represented by a 3D mesh to a desired orientation within a 3D coordinate system. The method includes receiving the 3D mesh in random alignment and changing an orientation of the 3D mesh to align the digital 3D model of teeth with a desired axis in the 3D coordinate system. The methods can also detect a gum line in the digital 3D model to remove the gingiva from the model.

8 Claims, 2 Drawing Sheets

(56) References Cited

U.S. PATENT DOCUMENTS

| | | | |
|---|---|---|---|
| 8,583,270 B2* | 11/2013 | Schneider | A61C 8/0077 700/118 |
| 2002/0015006 A1* | 2/2002 | Suzuki | A61B 6/032 345/6 |
| 2002/0064759 A1 | 5/2002 | Durbin et al. | |
| 2004/0096799 A1 | 5/2004 | Hughes et al. | |
| 2004/0197727 A1* | 10/2004 | Sachdeva | A61C 7/00 433/24 |
| 2005/0089214 A1 | 4/2005 | Rubbert et al. | |
| 2006/0120582 A1 | 6/2006 | Squilla et al. | |
| 2007/0024611 A1 | 2/2007 | Ingram | |
| 2008/0020341 A1* | 1/2008 | Krumbholz | G01J 3/462 433/26 |
| 2009/0162813 A1 | 6/2009 | Glor et al. | |
| 2009/0246726 A1* | 10/2009 | Chelnokov | A61C 7/002 433/24 |
| 2010/0145898 A1 | 6/2010 | Malfliet et al. | |
| 2010/0315419 A1 | 12/2010 | Baker | |
| 2012/0064489 A1* | 3/2012 | Rubbert | A61C 5/007 433/175 |
| 2013/0325431 A1 | 12/2013 | See et al. | |
| 2015/0305696 A1* | 10/2015 | Yamakawa | A61B 6/14 378/19 |

OTHER PUBLICATIONS

PCT International Search Report for PCT/US2015/047720, dated Dec. 7, 2015.

Dijkstra, "A Note on Two Problems in Connexion with Graphs," Numerische Mathematik, 1959, vol. 1, pp. 269-271.

D'Errico, "Understanding Gridfit", The Methodology of Gridfit, Dec. 28, 2006, pp. 1-6. [Retrieved from the internet on Nov. 19, 2014], URL<1.mathworks.com/matlabcentral/fileexchange/8998-surface-fitting-using-gridfit>, 6 pages.

Gerbrands, "On the Relationships between SVD, KLT and PCA", Pattern Recognition, 1981, vol. 14, No. 1-6, pp. 375-381.

* cited by examiner

METHOD OF ALIGNING INTRA-ORAL DIGITAL 3D MODELS

BACKGROUND

The use of digital 3D models in the dental market is becoming more prevalent. These models can be acquired in vivo using an intra-oral scanner or off-line by laser scanning of a traditional impression. The digital 3D models can be used tom various clinical tasks including treatment planning, and crown and implant preparation. The models can also be used in diagnostic aides, for example to assess tooth wear and gingival recession. The digital 3D models are usually obtained in a random orientation and not fixed to a particular coordinate system. Accordingly, a need exists to align intra-oral digital 3D models to a given coordinate system for diagnostic or other purposes.

SUMMARY

Methods for aligning a digital 3D model of teeth, consistent with the present invention, include receiving a digital 3D model of teeth represented by a 3D mesh in random alignment and changing an orientation of the 3D mesh to align the digital 3D model of teeth with a desired axis within a 3D coordinate system.

Methods for modifying and aligning a digital 3D model of teeth, consistent with the present invention, include receiving a digital 3D model of teeth with associated gingiva represented b a 3D mesh in random alignment, detecting a gum line in the digital 3D model, and removing the gingiva from the digital 3D model. The digital 3D model without the gingiva is aligned with a desired axis within a 3D coordinate system.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Figure 1:
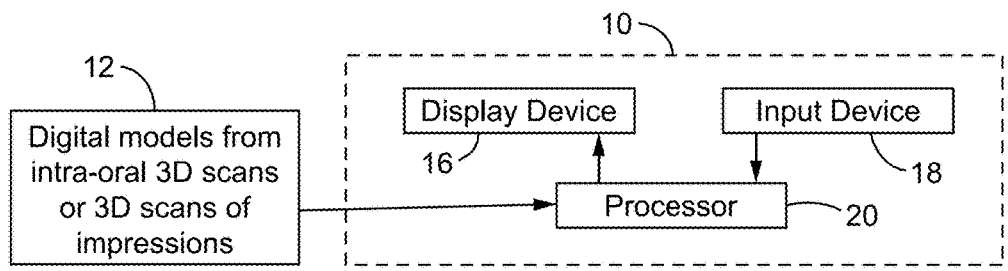
FIG. 1 is a diagram of a system for aligning digital 3D models based upon intra-oral 3D scans or 3D scans from impressions.
Figure 2:
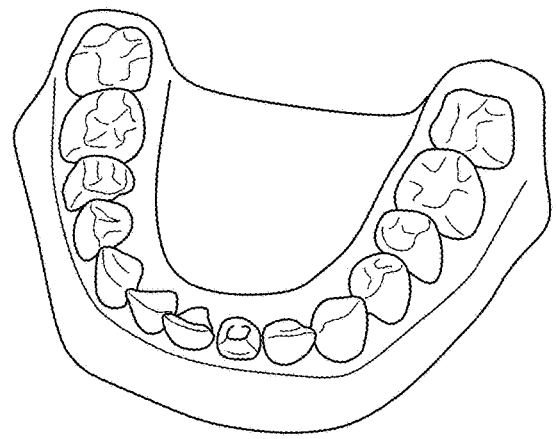
FIG. 2 illustrates a 3D model of teeth from intra-oral scans.

FIG. 1 is a diagram of a system 10 for aligning digital 3D models based upon intra-oral 3D scans. System 10 includes a processor 20 receiving digital 3D models of teeth (12) from intra-oral 3D scans or scans of impressions of teeth. System 10 also includes an electronic display device 16, such as a liquid crystal display (LCD) device, for displaying digital 3D models and an input device 18 for receiving user commands or other information. An example of digital 3D model of a patient's teeth from a scan is shown in FIG. 2. Systems to generate digital 3D images or models based upon image sets from multiple views are disclosed in U.S. Pat. Nos. 7,956,862 and 7,605,817, both of which are incorporated herein by reference as if full set forth. These systems can use an intra-oral scanner to obtain digital images from multiple views of teeth or other intra-oral structures, and those digital images are processed to generate a digital 3D model representing the scanned teeth. System 10 can be implemented with, for example a desktop, notebook, or tablet computer. System 10 can receive the 3D scans locally or remotely via a network.

The 3D scans addressed herein are represented as triangular meshes. The triangular mesh is common representation of 3D surfaces and has two components. The first component, referred to as the vertices of the mesh, are simply the coordinates of the 3D points that have been reconstructed on the surface i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Figure 3:
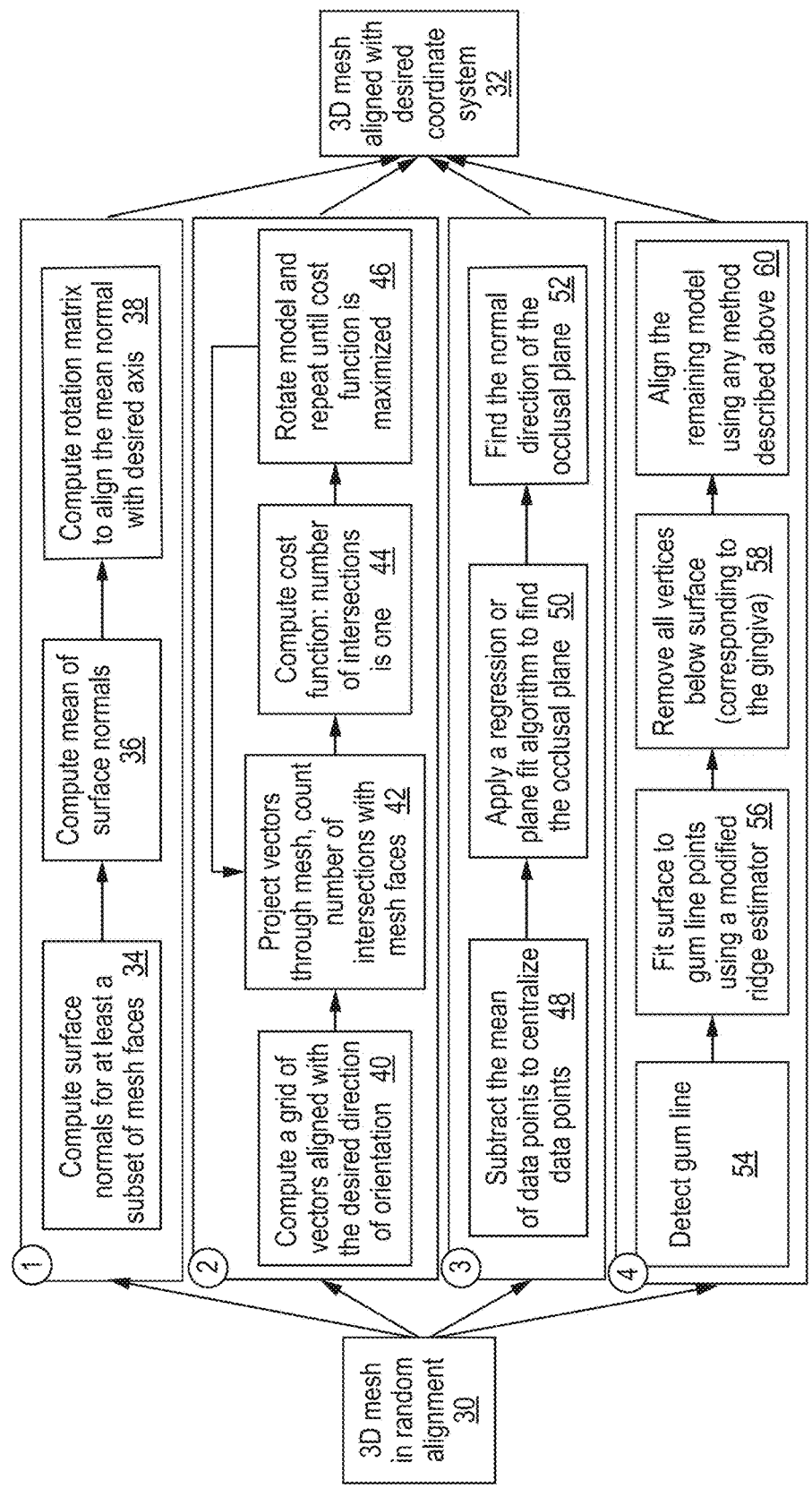
FIG. 3 is a flow chart of methods for aligning and modifying digital 3D models.

FIG. 3 is a flow chart of methods 1-4 for aligning digital 3D models and optionally removing the gingiva from the models. These methods can be implemented in software or firmware modules, for example, for execution by processor 20. These methods can alternatively be implemented in hardware modules or a combination of software and hardware. The methods 1-4 receive a 3D mesh in random alignment (step 30) and generate a 3D mesh aligned with a desired axis in a 3D coordinate system (step 32). The 3D mesh is triangular mesh having the components described above.

In one particular embodiment, the alignment results in an occlusal plane being aligned to a desired orientation within a 3D coordinate system. The occlusal plane can be determined by finding points at the top of a tooth or teeth in a digital 3D model of the teeth and fitting a plane to those points. In one example, a desired orientation aligns the occlusal plane with the Y axis with the teeth pointing up in the model, although the occlusal plane can also be aligned with other axes using the alignment methods. An example of a 3D coordinate system includes an X axis, a Y axis, and Z axis with each of the axes being mutually orthogonal with one another.

Alignment Method 1—Aggregation of Normals

Method 1 involves the following steps: compute the normals of the mesh at each face or vertex, or at a subset of the faces or vertices (step 34); compute an aggregate of the surface normals to determine a representative normal direction by calculating the mean of the surface normals or, alternatively, calculating the sum or the median of the surface normals (step 36) and compute and apply a rotation matrix to align the mean normal with a desired axis (step 38). There are several methods that can compute the rotation matrix between two vectors, the mean of the normals with the desired spatial orientation. The exemplary method below uses Rodrigues formula.

For two vectors a and b, one can find the axis of rotation x by computing the normalized cross product, and the angle between them, θ, as follows:

$$\lambda = \frac{a \times b}{\|a \times h\|}$$

$$\theta = \cos^{-1} \frac{a \cdot b}{\|a\| \cdot \|b\|}$$

Rodrigues' formula yields the rotation matrix [R] to transform from vector a to vector b.

$$[R]=[I]+x\sin\theta+x^2(1-\cos\theta)$$

Here [I] is the 3×3 identity matrix.

Table 1 provides exemplary pseudocode for implementing a alignment method 1.

TABLE 1

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: aligned mesh where the occlusal surface of the teeth are roughly parallel to the XZ plane and perpendicular to the vertical axis, in this case the Y axis.

Method steps:

1. For each vertex $v_i$ in V compute the normal direction $n_i$.
2. Compute the sum of normal vectors of all vertices and determine the direction as n_sum. Alternatively, the mean or median of the normal directions can be used.
3. Determine the direction and angle of rotation to align n_sum with desired axis (such as Y) using Rodrigues' fonnula as follows:
   a = n_sum b = Y
   direction of rotation: x = a × b / ||a × b||
   angle of rotation: $\theta = \cos^{-1}(a.b/||a||.||b||)$
   Where x denotes cross product and . denotes the dot product of vectors
   Rotation matrix to be applied to vertices:
   $[R] = [I] + x\sin\theta + x^2(1-\cos\theta)$

Alignment Method 2—Open Mesh Assumption

Method 2 involves the following steps: compute a grid of vectors aligned with the desired direction of orientation (step 40); project the vectors through the mesh and count the number of intersections with mesh faces (step 42); compute the cost function as the total number of cases, where the number of intersections for each grid line with faces on the mesh is one (step 44); and rotate the model and repeat steps 42 and 44 until the cost function is maximized (step 46).

This approach makes the assumption that the model represents an open topographic surface, i.e. the surface does not self-intersect or close on itself. This model is often the ease with 3D scans of dentitions. To compute the final transformation matrix, this method projects a set of parallel rays (also parallel to a fixed desired axis) onto the mesh; the grid spacing of those rays is chosen based on the model resolution and computational limitations. The cost function is a ratio of the number of rays that intersected one face to the number of rays that intersected more than one face:

$$f(\Theta) = \frac{\text{sum}(n == 1)}{\text{sum}(n > 1)},$$

n is the number of faces each ray passes through The method rotates the model around some given axis (θ) and maximizes the cost function until a local maximum is found.

Table 2 provides exemplary pseudocode for implementing alignment method 2.

TABLE 2

Input: a 3D mesh with a set of vertices V specified in 3D coordinate system X, Y and Z. Y represents the Vertical axis or the general direction in which the teeth point upwards. The mesh also has a set of triangulations or faces F based on the vertices.
Output: aligned mesh where the occlusal surface of the teeth are roughly parallel to the XZ plane and perpendicular to the vertical axis, in this case the Y axis.

Method steps:

1. Compute a grid of vectors parallel to the Y axis and spanning the XZ space of the input mesh, in particular uniformly sample min(X) to max(X) and min(Y) to max(Y) with vectors pointing, along Y axis.
2. Perform a rotation of the mesh by a chosen angle about X and Z axes.
3. Compute the number of vectors in the grid that intersect with exactly one face of the mesh as N.
4. Adjust the rotation angles about X and Z.
5. Repeat steps 2 to 4 until a maximum number of iterations or until the sum N in step 3 is maximized.

Alignment Method 3—Regression or Plane Fitting

Method 3 involves the following steps: subtract the mean of data points to centralize the data points (step 48): apply a regression or plane fit algorithm (e.g., Support Vector Regression (SVR) function) to find the occlusal plane (step 50); and find the normal direction of the occlusal plane (step 52). Alternatively, principal component analysis (PCA Robust PCA and other forms of regression such as Generalized Linear Models (GLM), Multivariate Regression can also be used.

This alignment method can be implemented using an SVR method to find the occlusal plane fitted to a mesh of the teeth in the digital 3D model. The alignment can be used to have the teeth in the digital 3D model essentially aligned with the Y axis. The alignment can use the LIBSVM toolbox and ϵ-SVR method. The kernel is chosen to be linear and ϵ5.

The best value of epsilon can be chosen based on many training meshes. The training is based en the assumption that teeth are roughly pointing up along the Y axis. The output is sample points from the occlusal plane which is given to a simple PCA method to find the normal direction. Alternatively, the SVR can also directly return the equation of the plane ca best fit. The normal direction can then be computed from this plane. SVR uses a linear loss function with a zero part within the margins which performs better for teeth dataset than the quadratic loss function in regular least square regression methods. It helps to decrease the effect of gingiva cut-lines which can be very jagged and bumpy in mesh scans. It also tries to rule out the vertical points on the teeth (buccal part) and give more weight of importance to the horizontal points on teeth (cuspal part) M determining the occlusal plane orientation. The RANSAC method and Robust PCA method can alternatively be used for the alignment.

Table 3 provides exemplary pseudocode for implementing alignment method 3.

TABLE 3

Input: a 3D mesh with a set of vertices V specified in 3D coordinate system X, Y and Z. Y represents the rough direction of vertical axis in which the teeth point upwards.
Output: the normal vector perpendicular to occlusal plane which represents the desired upward direction of teeth.
Assumptions: Teeth are roughly pointing up along the Y axis. The mesh has been truncated below the gum line.

Method steps:

1. Subtract the mean of data points to centralize the data points around (0, 0, 0).
2. Apply the SVR with linear kernel and margin value ε to find the occlusal plane.
3. Find the normal direction of the occlusal plane by geometrical methods or applying a simple PCA.

Alignment Method 4—Gum Detection and Semi-Removal

Method 4 involves the following steps: detect the gum line in the model using correlation on curvature or a classification function based upon mesh surface properties (step 54): fit a surface to the gum line points using a modified ridge estimator (step 56); remove all vertices below the surface corresponding to the gingiva (step 58); and align the remaining model using any of the above methods 1-3 (step 60). This method 4 can align the model before detecting the gum line and realign the model after guru line detection, or only align the model after gum line detection.

For step 54, alternatively a classifier using multiple surface features such as curvature, normal direction, mesh local covariance, or other such features can also be used to predict if a vertex lies on the gum line. Some examples of the classifiers are linear discriminant classifier, decision tree, support vector machines, and the like.

For step 56, the method detects most gum line points, not necessarily all gum line points, or at least a sufficient number of gum line points to fit a surface to the gum line.

Table 4 provides exemplary pseudocode for implementing alignment and gum line detection method 4 using alignment method 1.

TABLE 4

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: aligned mesh where the occlusal surface of the teeth are roughly parallel to the XZ plane and perpendicular to the vertical axis, this case the Y axis, and the mesh below the gum line is truncated.

Method steps:

1. Align mesh with aggregation of normals approach, as explained in method 1.
2. Compute curvature of each vertex on the mesh.
3. Compute boundary points of the mesh.
4. Compute vertex ring for every vertex, which is a matrix of connectivity
5. Gum line Detection: This method helps in alignment of scans of dentitions especially quadrant scans.
    i. Find gum line points.
        a. Iterate through every point along the border and follow it to the peak of the model storing the curvature at each point, referred to as a 1D curvature map.

TABLE 4-continued b. Uses an absolute value function as the template.
    c. Correlate template with curvature map, find peak. Discard if it is below some threshold.
  ii. Connect points for continuity.
    a. Expand gum line by including one additional connected vertex.
    b. Label each connected component of gum line vertices and score them based on the number of vertices connected.
    c. Perform Dijkstra's shortest path inversely weighted by curvature (low curvature vertices are highly weighted).
    d. Repeat step (ii)(c) until all segments have been connected, or the sum of the scores has been maximized.
6  Fit a surface to gum line points.
7  Remove portions below the surface (gingiva in the model) that intersect the mesh.
8  Realign the model with gingiva removed using aggregation of normals (method 1) or other alignment methods.

Figure 4:
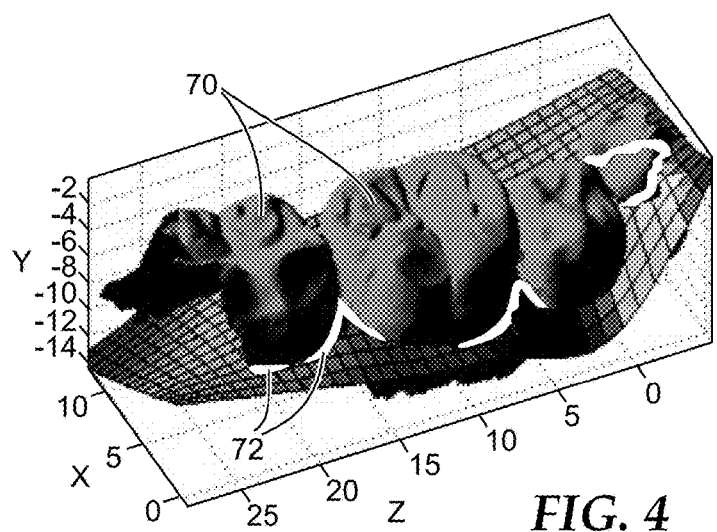
FIG. 4 is a diagram of a digital 3D model aligned in a desired orientation within a 3D coordinate system and with the gum line detected.

FIG. 4 is a diagram of a digital 3D model aligned with a desired orientation and with the gum line detected. For example, the digital 3D model of teeth 70 has been aligned with the Y axis (teeth pointing up along with Y axis), and the gum line 72 has been identified with portions of the gingiva below gum line 72 removed from the digital 3D model. In this example, the alignment results in a desired orientation of the occlusal plane generally parallel with or extending along, the XZ plane and perpendicular to, or intersecting with, the Y axis.

The invention claimed is:

1. A method for aligning a digital 3D model of teeth, comprising steps of:
receiving a digital 3D model of teeth represented by a 3D mesh in random alignment;
computing a grid of vectors aligned with a desired axis within a 3D coordinate system;
projecting the vectors through the mesh to count a number of intersections of the vectors with faces of the mesh;
computing a cost function for the mesh based upon the number of intersections; and
rotating the mesh and repeating the projecting and the computing the cost function steps until the cost function is maximized to align the mesh with the desired axis,
wherein the computing the cost function step comprises computing as the cost function $f(\theta)=(\text{sum}(n==1)/\text{sum}(n>1))$, where $\theta$ is the desired axis, and n is a number of the faces each of the vectors intersects.

2. A system for aligning a digital 3D model of teeth, comprising:
a module for receiving a digital 3D model of teeth represented by a 3D mesh in random alignment;
a module for computing a grid of vectors aligned with a desired axis within a 3D coordinate system;
a module for projecting the vectors through the mesh to count a number of intersections of the vectors with faces of the mesh;
a module for computing a cost function for the mesh based upon the number of intersections; and
a module for rotating the mesh and repeating the projecting and the computing the cost function until the cost function is maximized to align the mesh with the desired axis,
wherein the computing the cost function module comprises a module for computing as the cost function $f(\theta)=(\text{sum}(n==1)/\text{sum}(n>1))$, where $\theta$ is the desired axis, and n is a number of the faces each of the vectors intersects.

3. The method of claim 1, wherein the rotating step comprises rotating the mesh around the axis $\theta$ until the cost function is maximized.

4. The system of claim 2, wherein the rotating module comprises a module for rotating the mesh around the axis $\theta$ until the cost function is maximized.

5. The method of claim 1, wherein the vectors are parallel with the desired axis.

6. The method of claim 1, wherein a grid spacing of the vectors is chosen based on a resolution of the digital 3D model.

7. The system of claim 2, wherein the vectors are parallel with the desired axis.

8. The system of claim 2, wherein a grid spacing of the vectors is chosen based on a resolution of the digital 3D model.

* * * * *